(12) United States Patent
Borden

(10) Patent No.: US 8,029,575 B2
(45) Date of Patent: Oct. 4, 2011

(54) POROUS AND NONPOROUS MATERIALS FOR TISSUE GRAFTING AND REPAIR

(75) Inventor: Mark Borden, Collegeville, PA (US)

(73) Assignee: Globus Medical, Inc., Audubon, PA (US)

( * ) Notice: Subject to any disclaimer, the term of this patent is extended or adjusted under 35 U.S.C. 154(b) by 881 days.

(21) Appl. No.: 11/552,244

(22) Filed: Oct. 24, 2006

(65) Prior Publication Data

US 2007/0093912 A1 Apr. 26, 2007

Related U.S. Application Data

(60) Provisional application No. 60/729,926, filed on Oct. 25, 2005.

(51) Int. Cl.
*A61F 2/02* (2006.01)
(52) U.S. Cl. .......... 623/23.73; 623/23.75; 606/907; 606/908
(58) Field of Classification Search .......... 606/76–77, 606/61, 246–249; 623/17.11–17.16, 23.55–23.63, 623/23.51, 23.75
See application file for complete search history.

(56) References Cited

U.S. PATENT DOCUMENTS

| | | | |
|---|---|---|---|
| 5,120,340 A | 6/1992 | Ducheyne et al. | |
| 5,866,155 A | 2/1999 | Laurencin et al. | |
| 6,077,989 A * | 6/2000 | Kandel et al. | 623/13.17 |
| 6,224,630 B1 * | 5/2001 | Bao et al. | 623/17.16 |
| 6,240,926 B1 * | 6/2001 | Chin Gan et al. | 128/898 |
| 6,530,956 B1 * | 3/2003 | Mansmann | 623/18.11 |
| 2004/0138758 A1 * | 7/2004 | Evans et al. | 623/23.51 |
| 2005/0209704 A1 | 9/2005 | Maspero et al. | |
| 2006/0121084 A1 * | 6/2006 | Borden et al. | 424/426 |

OTHER PUBLICATIONS

Robinson BP, et al., Calvarial Bone Repair with Porous D,L-polylactide., Otolaryngol Head Neck Surg. Jun. 1995; 112(6):707-13.
Kokubo, T et al., Solutions Able to Reproduce In Vivo Surface-structure Changes in Bioactive Glass-ceramic A-W3, J. Biomed. Mater. Res. vol. 24, No. 6, pp. 721-734. Jun. 1990.
Murphy et al., Growth of Continuous Bonelike Mineral Within Porous Poly (lactide-co-glycolide) Scaffolds in vitro., J. Biomed Mater Res., Apr. 2000; 50(1):50-8.
International Search Report and Written Opinion dated Mar. 3, 2008, PCT/US 06/60221.
International Preliminary Report on Patentability dated May 8, 2008, PCT/US 06/60221.

* cited by examiner

*Primary Examiner* — Eduardo C Robert
*Assistant Examiner* — Christina Negrelli

(57) ABSTRACT

Implants, such as interbody spacers, fusion devices and bone grafts, are provided having improved mechanical properties and/or degradation profiles. Such implants include a three-dimensional scaffold formed from particles, such as microspheres, which may in some embodiments be resorbable or biodegradable and which may have at least two different degradation rates. In some embodiments, the scaffold may be elastomeric. The three-dimensional scaffold may be for example, porous or semi-porous. Also provided are kits including such implants, and methods of producing and using the same.

33 Claims, 6 Drawing Sheets

POROUS AND NONPOROUS MATERIALS FOR TISSUE GRAFTING AND REPAIR

RELATED APPLICATION

This patent application claims the benefit of priority to U.S. Provisional Patent Application No. 60/729,926 filed on Oct. 25, 2005, entitled "Method of Fabricating Porous and Non-Porous Implants for Structural Grafting Applications." The content and subject matter of this provisional patent application are hereby incorporated by reference in their entireties, including all text and figures.

FIELD

Exemplary embodiments of the present invention are generally directed to devices including three-dimensional scaffolds and/or composites having improved mechanical properties and/or degradation profiles, and methods of producing the same. Exemplary embodiments also include kits and systems including such devices in various forms, such as implants including for example, synthetic bone grafts, bone graft onlays, interbody spacers, and disc repair. Exemplary embodiments further include methods of treating a patient, which include inserting into a patient in need thereof, a scaffold and/or composite formulated into a desired device.

BACKGROUND

Bone grafts used in current orthopaedic and neurosurgery procedures often serve two different functions. In certain surgical indications a graft is needed to act as a scaffold to aid the new bone in completely bridging a defect. In this type of graft, the material is typically porous to allow for bone ingrowth into the graft. Porous bone grafts act as a scaffold or trellis that allows regenerating bone to heal across a defect that it normally could not. Cancellous bone and porous ceramics have typically been used as bone graft scaffolds. Structural grafts, on the other hand, are bone graft materials whose main function is to mechanically support the site and add stability during the healing process. These materials have little to no porosity but have the strength necessary for stabilization. Cortical bone struts, rings, and wedges are common examples of structural grafts.

The source of the bone-derived grafts is either from the patient's own cancellous or cortical bone (autograft) or from tissue donors (allograft). Although these bone grafts have been successfully used over the years, they are not devoid of certain disadvantages. Removing healthy bone from the patient and placing at another site often results in complications of pain and infection at the donor site. Using a tissue donor can result in variable resorption characteristics and unpredictable structural integrity. In an attempt to avoid the problems of autograft and allograft, synthetics have become a popular choice for orthopedic surgeons. Resorbable polymers, ceramics, and composites have been shown to be effective substitutes for bone derived grafts without any of the autograft or allograft related complications.

From a scaffold standpoint, current porous implants are used as graft materials primarily for bone and cartilage repair. These scaffolds are characterized by a high percent porosity to allow for bone and/or cartilage in-growth. A variety of pore forming techniques used to create three-dimensional porous scaffolds are known. These techniques, however, result in structures that can be easily crushed or deformed due to their low strength. In orthopedic grafting procedures, surgeons often use force to impact the graft material into the site, which may crush or fracture the graft material. Thus, if the graft material has low mechanical properties, the porosity can be significantly reduced or completely eliminated if the graft is crushed or fractured during or after the surgical procedure. With little to no porosity remaining, the graft can no longer function as a scaffold for tissue in-growth. Therefore, it would be advantageous to create a tissue scaffold with higher strength to prevent crushing during the implantation procedure.

For structural grafting applications, current implants are typically composed of non-degradable materials such as titanium, poly(ether ether ketone) [PEEK], and polyethylene. Although these high strength materials possess the required mechanical properties, their function is only required during the healing process. Once the site has fully healed, the implant serves no purpose and can be a source of long term complications such as loosening or failure. This has driven the search for resorbable implants that perform their mechanical function and are then resorbed by the body. Polymers such as poly (lactic acid) (PLA) and poly (lactide-co-glycolide) (PLG) have been widely used to create resorbable implants for structural applications such fracture fixation, reconstruction, and spinal fusion. However, one issue with typical resorbable polymer implants is that they maintain their volume until the very end of resorption. This can lead to a void in the tissue that may or may not eventually fill in. It would be advantageous to have a material that would allow tissue in-growth into the implant prior to complete resorption of the device.

SUMMARY

Exemplary embodiments of the present invention are generally directed to improving mechanical properties of devices, such as porous scaffolds and composites, which may be formed for example, into an implant suitable for insertion into a patient. With improved mechanical properties, the devices can resist impaction grafting without significant deformation or destruction of the device.

Exemplary embodiments of the present invention are also generally directed to devices, such as implants, having a step-wise degradation profile that allows for tissue in-growth into the implant after insertion into a patient. This allows for improved replacement of the resorbable device by surrounding tissue.

Exemplary embodiments of the present invention are also generally directed to creating porous scaffolds from elastomeric materials so that the implant can support dynamic loading as well as allow for soft tissue ingrowth. With elastomeric properties and a porous structure, the implant would be capable of supporting cyclic loading such as in the spine while allowing tissue growth into the device to form an interface that would prevent device migration.

Other example embodiments include methods of making such devices, kits and systems including such devices, and methods of treating patients by inserting implants into a patient in need thereof.

BRIEF DESCRIPTION OF THE DRAWINGS

Embodiments of the invention are herein described, by way of non-limiting example, with reference to the following accompanying drawings.

DETAILED DESCRIPTION

Figure 1:
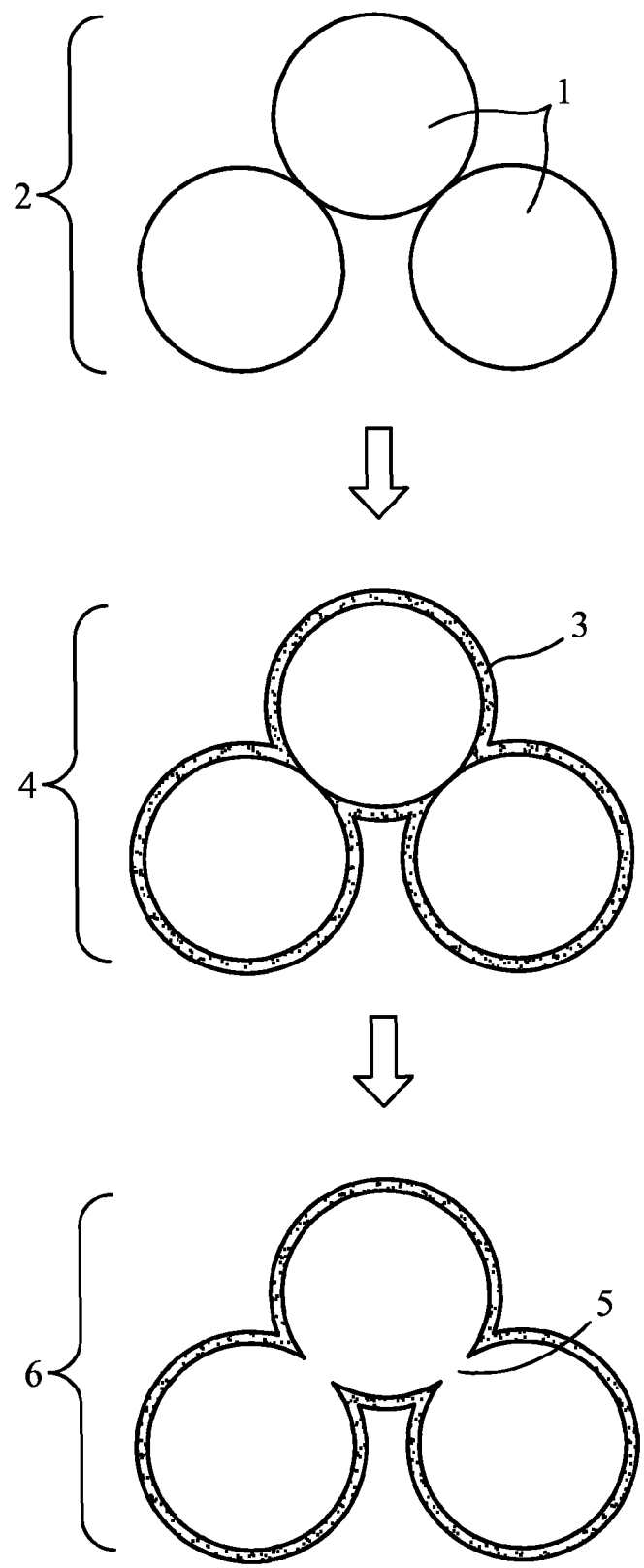
FIG. 1 is a schematic of a thermal consolidation process in accordance with non-limiting example embodiments.

The aspects, advantages and/or other features of example embodiments of the invention will become apparent in view of the following detailed description, which discloses various non-limiting embodiments of the invention. In describing example embodiments, specific terminology is employed for the sake of clarity. However, the embodiments are not intended to be limited to this specific terminology. It is to be understood that each specific element includes all technical equivalents that operate in a similar manner to accomplish a similar purpose. Additionally, all of the citations herein are incorporated by reference in their entirety.

Example devices may be adapted for many different purposes and are not intended to be limited to the specific example purposes set forth herein. By way of non-limiting example, devices may include porous polymer scaffolds that may be used for musculoskeletal repair. Other non-limiting examples of such devices are composites that may be used, for example, for structural grafting. Those skilled in the art would be able to adapt the devices of the present invention, depending for example, on the intended use of the device, e.g., by selecting the materials including materials having two, three or more multiple resorption rates or degradation profiles.

DEFINITIONS

As used herein, "a" or "an" may mean one or more. As used herein, "another" may mean at least a second or more.

The terms "particle," "particulate," "sphere," and "microsphere" are used interchangeably herein and are intended to encompass polymer particles that begin somewhat discrete from one another before the methods herein are performed. These terms are also intended to include such particles after they are sintered, melted or otherwise bonded to one another for example to form a scaffold, although their shape may change. These terms are also intended to include such particles, regardless of shape and even if they are compressed to become for example, somewhat elongated in shape. Accordingly, the terms "particle," "particulate," "sphere," and "microsphere" are intended to be very broad and encompass many shapes, including spheres, spheroids, rods, pellets, granules, blocks, grains or any other suitable shape.

As used herein, a "scaffold" is a device or portion thereof that allows the ingrowth of tissue within or upon the surface of the device. A scaffold may be a temporary device, which may be mostly or entirely resorbed by the body of a patient having a scaffold implanted therein. In such embodiments, tissue eventually takes up at least a portion of physical space occupied by the scaffold.

A "composite" is a device or portion thereof made of distinct portions. According to example embodiments, composites may include two or more portions having different resorption profiles, that is each portion resorbs at a different rate than the other distinct portions.

A "resorbable" material may include for example ceramics, polymers or other materials that are designed to be resorbed by the body of a patient, and eventually replaced with healthy tissue. The terms "degradation rate," "degradation profile," "resorption rate," and "resorption profile" are all used somewhat interchangeably herein and are intended to refer to the time over which a resorbable material is resorbed by the body. The relative terms "fast" and "slow" are used herein to refer to the relative resorption rate of resorbable materials with respect to each other. For example, according to some embodiments, multiple materials may be used, where one material has a so-called "fast" resorption rate and another material has a so-called "slow" resorption rate. Those skilled in the art need not know the actual resorption rates (which may vary somewhat depending on various factors such as material selection, placement location in the body, temperature, surrounding tissue, etc.) to understand that these embodiments are intended to include at least two discrete portions having material compositions that separately degrade or resorb at different rates than one another, i.e., one composition resorbing faster than the other(s).

As used herein, "biocompatible" means the ability of an object to be accepted by and to function in a patient without eliciting a significant foreign body response (such as, for example, an immune, inflammatory, thrombogenic, or like response).

As used herein, "polymer" means a chemical compound or mixture of compounds formed by polymerization and including repeating structural units. Polymers may be constructed in multiple forms and compositions or combinations of compositions. The term "polymer" is also intended to cover copolymer materials and polymer blends formed from two or more polymers. Examples of suitable polymers that may be used include, but are not limited to, biocompatible and/or bioabsorbable polymers or copolymers and combinations thereof. Non-limiting examples include, poly(hydroxy acids), poly (phosphazenes), poly(amino acid-carbonates), poly(anhydrides), and poly(urethanes).

One of ordinary skill in the art will appreciate that the selection of a suitable polymer or copolymer depends on several factors. For example, factors in the selection of the appropriate polymer(s) that is used may include bioabsorption (or bio-degradation) kinetics; in vivo mechanical performance; cell response to the material in terms of cell attachment, proliferation, migration and differentiation; and biocompatibility. Other relevant factors, which to some extent dictate the in vitro and in vivo behavior of the polymer, include the chemical composition, spatial distribution of the constituents, the molecular weight of the polymer, and the degree of crystallinity. The selection of polymer materials having varying resorption profiles would allow a multi-phase implant to degrade in a step-wise manner, thus allowing for gradual tissue in-growth. Standard techniques used in the art such as varying molecular weight, copolymer ratio, and crystallinity can be used to further differentiate degradation properties of the polymers.

As used herein, "porosity" means the ratio of the volume of interstices of a material to a volume of a mass of the material.

The term "porous scaffold" refers to a structural matrix, which includes a solid region and an open porous region comprising spaces or discontinuities between adjacent areas of the solid region. The open porous region may be filled with air or gas at least initially, or it may be at least partially filled with liquid, solid particles, gel, and the like.

It should be understood that the macropores within the scaffold can simply be void spaces filled with air or gas. It is also within the scope of the invention to at least partially fill some or all of the void spaces with a liquid, gel or solid (e.g., a plurality of particles such as a fine powder). The liquid, gel or solid may include one or more active agents. According to some embodiments, one or more active agents may be coated on, or otherwise incorporated into, the scaffold. By way of non-limiting example, such "active agents" may include an antibiotic substance, growth factors, cellular coatings, and/or other biologically active substances. Thus, the biocompatible and biodegradable implant, when implanted into a cavity or extraction wound not only fills the cavity but also permits the controlled release of biologically active substances. For example, the substance within the pores may be selected such that bacterial growth is hindered, bone formation is accelerated, and/or pain at the bone wound is reduced.

It is also within the scope of the invention to prepare an implant comprising a shaped composite that may include few, if any, macropores (e.g., by using sufficient material to fill some or all void spaces and create a solid composite).

Devices Having Improved Mechanical Properties

Example embodiments include devices such as implants, which may be advantageous for example, for structural graft applications. Such devices may include those comprising polymer particles bonded together to form all or part of a scaffold or composite. Thus, methods include providing a plurality of particles and bonding the particles together to form a scaffold. The particles may be bonded together for example, by heating, solvents, and/or the use of adhesives.

In particular, exemplary embodiments include a three-dimensional scaffold made by a compression technique that includes providing a plurality of particles; compressing the particles; and bonding the particles together to form a scaffold. Compressing the scaffold may alter the shape of the particle, for example, making them more of an elongated shape, which may serve to increase the bonding area between the particles and increase the strength. The plurality of particles may include two or more particles having different shapes and/or sizes. According to example embodiments, the particles may be bonded together using heat. The compression and heating may be performed at different times, e.g., compressed prior to heating, or the particles may be compressed during heating. The compression of the particles may also be done in a controlled manner to compress the particles to a specific height. The compressed height is then essentially maintained throughout the heating process. The term "heating" is intended to include for example, heating to a temperature above the polymer's glass transition temperature but below its melting point, by any suitable method available to those skilled in the art. This compression and heating process is referred to herein as a "particle compression" process. Methods implementing a "particle compression" process may include for example, providing a plurality of particles, compressing the particles, and sintering the particles together with heat to form a scaffold.

Further, the particles can be subjected to a compressive load during heating so that the load compresses the particles to a specific height. A heating mold can be designed to stop the compression once the desired height is obtained. Further non-limiting embodiments are discussed in Example 1 below.

Example methods for producing a three-dimensional scaffold include coating a porous scaffold with a thermally stable material; and heating the coated scaffold past the melt temperature of the scaffold and under the melt temperature of the thermally stable material, to thermally consolidate the scaffold. This coating and heating process is referred to herein as a "thermal consolidation" process. The porous scaffold may be a porous polymer structure, e.g., a structure of particles that may be at least partially bonded (e.g., sintered) together, or simply touching one another, but not bonded.

Particles in any of the processes herein may include for example, particles comprising at least one resorbable polymer, biocompatible polymer, and/or copolymers. The particles may each comprise essentially the same composition, or scaffolds may include particles having two or more compositions, such as compositions having different shapes and sizes, and/or different resorption profiles as described further herein.

Further exemplary methods for producing a three-dimensional scaffold may include creating a three-dimensional, porous polymer structure; coating the porous polymer structure with a thermally stable material; and heating the coated structure above the melt temperature of the underlying polymer and under the melt temperature of the thermally stable material to thermally consolidate the porous polymer structure. According to example embodiments, the heating may include repeated heating and cooling at controlled rates to anneal the polymer. The porous polymer structure may be for example, a plurality of particles sintered together to form a scaffold.

Methods that include thermal consolidation may further include removing the thermally stable material after heating. Alternatively, depending on the intended use of a resulting device, the thermally stable material may be left in place within the scaffold.

Examples of thermally stable material may include one or more resorbable polymers, resorbable copolymers, resorbable polymer blends, or resorbable ceramics. The thermally stable material does not substantially melt or deform at the melting point of the scaffold. The thermally stable material may include one or more biologically active agents such as growth factors, cells, and blood factors. The coating process may include filling essentially the entire porosity of the scaffold or structure with a thermally stable material, or it may include coating the surface of the scaffold (e.g., coating individual particles) while essentially retaining the scaffold's porosity.

According to example embodiments, the plurality of particles may be added to a separate structure such as a mold or implant either before or after forming the scaffold. According to example embodiments, the particles may be added to the structure and are bonded (e.g., by sintering the particles together or compressing and/or heating) to form a scaffold within the structure. The structure may include for example, a mold that may be removed after formation of the scaffold, or it may include an implant, such as an intervertebral spacer, interference screw, fracture screw, rod, suture anchor, or plate, such that the scaffold makes up only a portion of an implant to be inserted into a patient.

According to some embodiments, the particles may be sintered, compressed and/or heated within a mold. According to example embodiments the resulting scaffold may be removed from the mold or the mold removed from the scaffold. Particle scaffolds or structures formed in a mold may form a device such as an implant themselves, e.g., an interbody spacer, or alternatively particle scaffolds may be included, embedded, or otherwise associated with, a substrate to form an implant. According to some embodiments, particle scaffolds may be formed directly within a device. In cases where particle scaffolds are formed in or incorporated into a device, the scaffold may serve to allow tissue in-growth into the device that previously did not allow tissue in-growth or did not allow in-growth to the same degree that the inclusion of such scaffolds will facilitate. A non-limiting example of a particle scaffold within an implant device is described in Example 2 below. The substrate or device itself may be resorbable, non-resorbable, or partially resorbable.

FIG. 1 is a schematic of a thermal consolidation process in accordance with non-limiting example embodiments. In this example, multiple polymer particles 1 form a sintered particle scaffold 2, which is shown as the starting three-dimensional structure. After the structure is coated with a thermally stable material 3, the coated structure 4 is heated past the melt temperature of the polymer phase. This causes the polymer phase of the original structure to liquefy into a highly viscous melt under the layer of the thermally stable coating. However, the outer stable coating essentially maintains the three-dimensional structure of the original scaffold and prevents the collapse of the melted polymer phase. In a molten state, the polymer consolidates into a single-continuous phase 5. The consolidation of the particles into a single phase improves the strength of the overall structure without altering the porosity. The consolidated particle scaffold 6 is then cooled below the melt temperature of the polymer phase and the thermally stable coating can be left in place or subsequently removed to result in a consolidated polymer structure.

Figure 2:
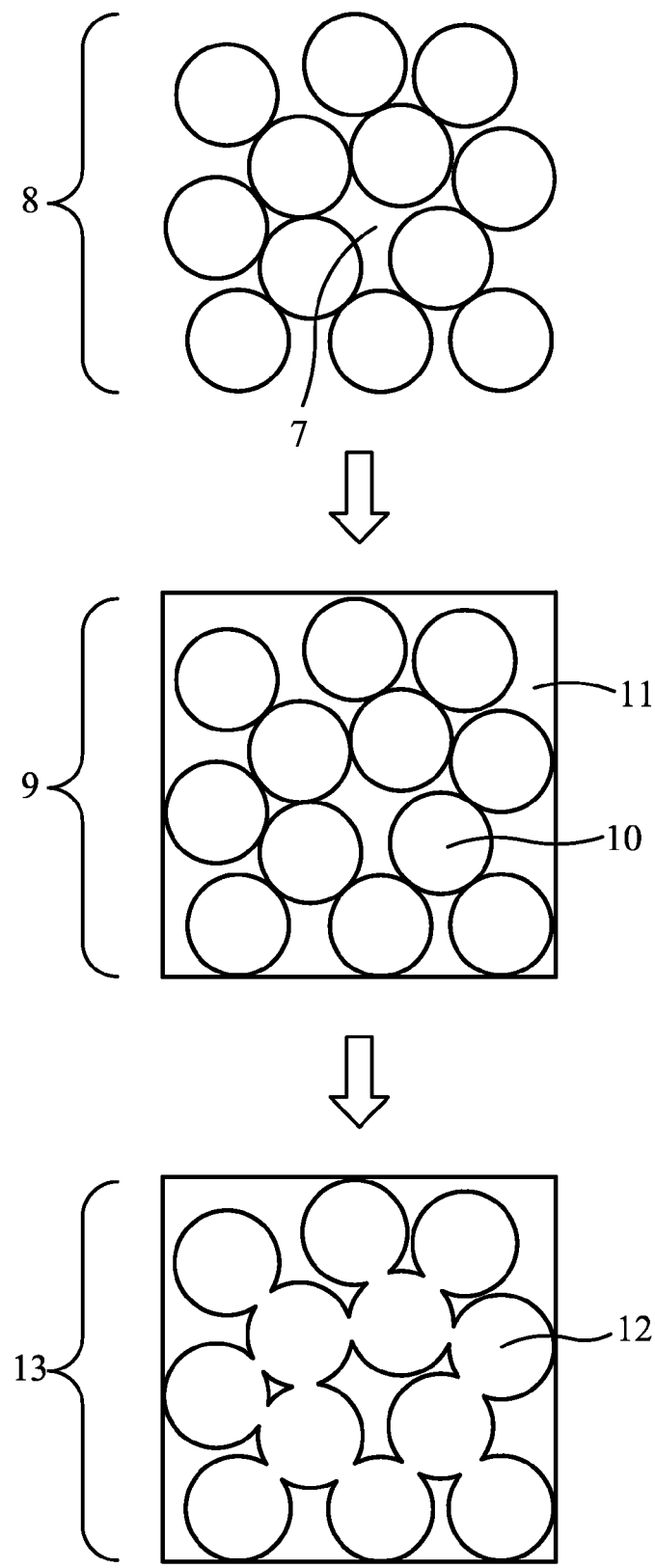
FIG. 2 is an illustration of the formation of a high strength composite in accordance with non-limiting example embodiments.

FIG. 2 is an illustration of the formation of a high strength composite in accordance with non-limiting example embodiments, which may be used, for example, for structural grafting. As shown in FIG. 2, a thermally stable material, such as a ceramic, in this case calcium cement, is added to the porosity 7 of a particulate scaffold 8. The resulting composite 9 is then subjected to thermal consolidation, that is, the composite is heated to at least the melt temperature of the polymer 10, but below the melt temperature of the ceramic 11, to melt the polymer phase and fuse the particles together 12 within a consolidated particulate composite 13.

After consolidation is complete, the thermally stable material may be maintained in the porosity to create a high strength composite as depicted in FIG. 2. This composite may then be machined into a variety of implants that would have improved properties such as increased strength. In addition, if the materials have different resorption profiles, resorption of one material before the other will give the composite the ability to support tissue ingrowth. This type of composite can function, for example, as a high strength structural graft used in fracture repair, spinal fusion, or other load bearing grafting applications. If the thermally stable material is used as a coating, then the porosity may be maintained and the material can be used for example, as tissue regeneration scaffold.

In non-limiting exemplary embodiments, a sintered PLA particulate scaffold may be filled with calcium phosphate material such as a hydroxyapatite, TCP, calcium carbonate, or calcium sulfate cement. Typical calcium cements undergo a phase transformation from liquid to solid. In the liquid state, a calcium cement can be added to the porosity of a porous PLA scaffold using vacuum or high pressure impregnation techniques. Once the cement hardens within the porosity of the particulate scaffold, the polymer-ceramic composite would be heated to the melting point of the polymer to consolidate the particulate phase. The resulting high strength composite could then be machined into implants of various types such as, but not limited to, interbody fusion cages, foot and ankle fusion cages, bone graft struts, structural augments compatible with hip and knee arthroplasty hardware, intramedullary rods, femoral rods, fracture rods, fracture screws, fracture tacks, suture anchors, and interference screws for anterior cruciate ligament (ACL) repair.

For polymer scaffolds, consolidation of the polymer phase can have several effects on the structure depending on the technique employed. If a sintered particle technique is used to create the three-dimensional scaffold, consolidation of the polymer phase through melting may significantly improve the particle-to-particle interface.

Figure 3:
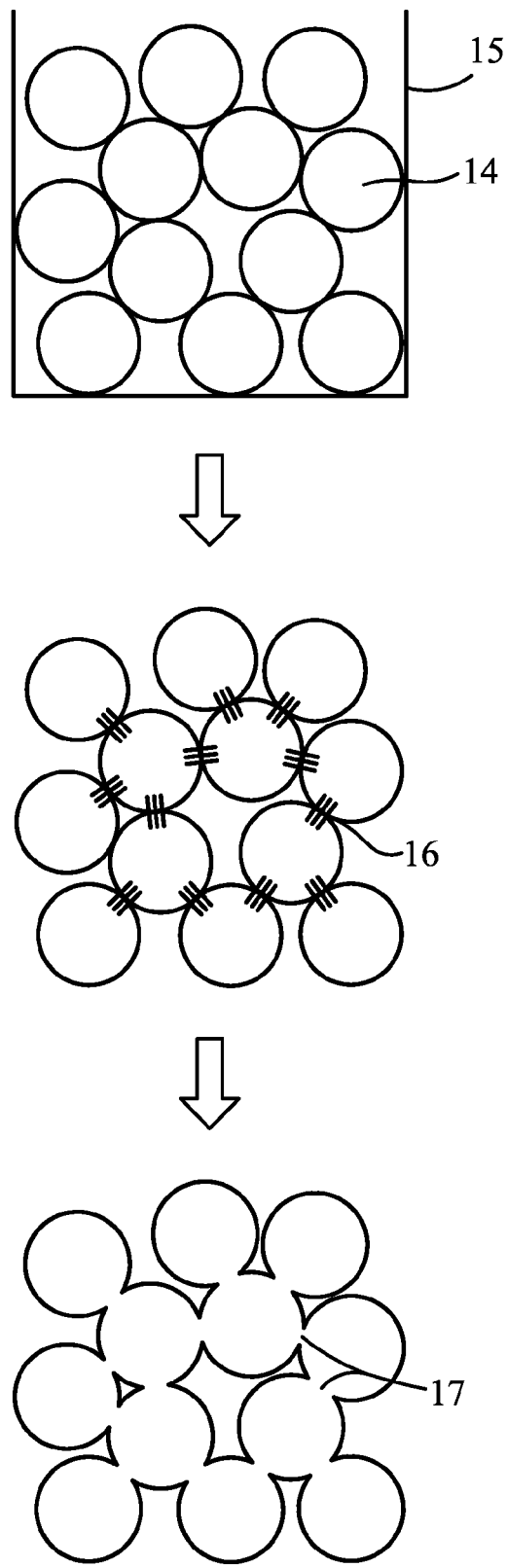
FIG. 3 is an illustration of effects of sintering and consolidation in accordance with non-limiting example embodiments.

FIG. 3 is an illustration of effects of sintering and consolidation in accordance with non-limiting example embodiments. As depicted in FIG. 3, loose polymer particles 14 are packed into a mold 15 and heated past the glass transition temperature of the polymer. After the scaffold is removed from the mold 15, the sintered particles maintain their three-dimensional structure through weak bonding at the particle contact points 16. These bonds are the result of minor polymer chain interactions between each particle. However, when the polymer phase is melted during a thermal consolidation technique, the particles consolidate into a mass 17 while essentially maintaining the scaffold shape. Thus, following consolidation, the melting of the polymer phase replaces the weak sintered polymer chain interactions with a much stronger thermal bond between the particles and significantly improves the overall strength of the polymer scaffold. Since the coating prevents the structure from collapsing while in a molten state, the porosity is maintained.

As indicated above, according to example embodiments, polymer scaffolds may be created by coating a porous structure with a thermally stable material that will not melt at the underlying polymer's melt temperature. As shown for example, in FIG. 1, the function of the coating is to maintain the porous structure and prevent its collapse when the underlying polymer substrate is melted and consolidated.

The process of coating the thermally stable material over the porous structure may include one or more of a variety of techniques commonly known to those skilled in the art. For example, Kokubo et al., "Solutions able to reproduce in vivo surface-structure changes in bioactive glass-ceramic A-W." J. Biomed. Mater. Res. 24:721-734, (1990), and Mooney et al., "Growth of continuous bonelike mineral within porous poly (lactide-co-glycolide) scaffolds in vitro." J. Biomed. Mater. Res. 50:50-58 (2002), disclose methods for creating solutions of simulated body fluid capable of precipitating calcium phosphate ceramics of the surface of ceramics and polymers. A variety of techniques can be used to coat the thermally stable material to the porosity of the scaffold. By way of non-limiting example, coating may include at least one method selected from dip coating or solution dipping, injection molding, precipitation, vacuum impregnation, and direct application. According to example embodiments, the coating can be as thin as 2-5 μm or can completely fill the porosity.

The thermally stable material may include for example a calcium-based material, such as a calcium ceramic material. For example, the thermally stable material may include one or more materials selected from hydroxyapatite, calcium sulfate, calcium carbonate, tricalcium phosphate, biphasic calcium phosphate, and calcium sodium sulfate. In further example embodiments, the coating may be a 2-10 μm layer of poorly crystalline hydroxyapatite precipitated from a solution of simulated body fluid. In other example embodiments, a porous scaffold may be dipped coated in a low viscosity mixture of calcium sulfate hemihydrate and water (in a ratio of about 1:1, 2:1 or 3:1 calcium sulfate hemihydrate to water).

In exemplary embodiments, the coating may be a biocompatible, resorbable polymer that has a melting point higher than the underlying polymer in the scaffold. Once the coating is applied, the coated structure may then be heated to melt and consolidate the underlying polymer phase into a single mass. The polymer is then cooled into a uniform structure. The consolidated structure may be then annealed through additional controlled heating and cooling steps to further improve the strength of the polymer.

In exemplary embodiments, once the polymer substrate is consolidated through the heating and cooling process, the coating may remain to function as an improved surface for tissue growth. With regard to bone grafting, for example calcium coatings may remain on the surface to promote bone cell attachment.

In other example embodiments, the coating may be removed to expose the underlying polymer scaffold and allow for thermal molding. In example embodiments, coatings based on calcium ceramics may be removed with exposure to mild acids such as acetic acid or 0.5 N hydrochloric acid. Polymer based coating may be removed by exposure of the coating to a solvent that will dissolve the coating only and not the underlying scaffold. In scaffolds where the coating is removed, the consolidated polymer scaffold may exhibit significantly improved mechanical properties over scaffolds that have not been thermally consolidated. This would occur without a change in the structure and porosity of the scaffold.

According to some embodiments, the coating may be soluble in a solvent that will not substantially dissolve the polymer scaffold. In these embodiments, the polymer coating may be applied as a solution to the scaffold such that it coats the surface of the polymer substrate without entirely blocking the porosity. The solvent may be evaporated and the coating dried on the surface of the porous structure. A two-phase polymer structure as described further herein, may then heated past the melting point of the scaffold but below the melting point of the coating. Once consolidated, the coating may remain or be removed for example, through dissolution in the coating's solvent.

In other exemplary embodiments, thermal consolidation can be used to create elastomeric structures, which may be useful for example, for grafting applications subjected to dynamic loading. Such applications may include, but are not limited to, cartilage repair, ligament repair, spinal disc repair, vascular grafting, tendon grafting, nerve grafting, spinal disc replacement, nucleus pulposus replacement, and facet joint replacement. In these embodiments, devices can comprise, for example, resorbable or non-resorbable materials that possess elastomeric properties. For example, particles may comprise one or more resorbable or non-resorbable elastomeric materials. By way of non-limiting example, such materials may include silicone, hydrogels, polyurethane or any polymers or copolymers exhibiting "rubbery" properties, the selection of which would be within the ability of one skilled in the art.

By way of example, suitable elastomeric polymers include those that exhibit a high percent elongation and a low modulus, while possessing good tensile strength and good recovery characteristics. In example embodiments, the elastomer may exhibit a percent elongation of greater than about 200%. In addition to these elongation and modulus properties, suitable elastomers may also have a tensile strength greater than about 4 MPa, or and a tear strength of greater than about 50 lbs/inch, or greater than about 80 lbs/inch.

In some examples of these embodiments, the elastomeric material can be formed into particles, which are bonded together to form a scaffold structure. The structure may then be coated with a thermally stable material and heated to consolidate the elastomeric phase. The coating would then be removed to result in a porous scaffold that would essentially possess the elastomeric properties of the starting material. This type of flexible scaffold may allow for tissue in-growth, in addition to providing dynamic load support to an implantation site.

In accordance with example embodiments, devices comprising polymer scaffolds may be adapted such that they are capable of becoming flexible upon heating and become more rigid upon cooling. By way of example, the use of thermoplastic polymers as the scaffold material will allow for custom shaping at the time of surgery. Shaping can be accomplished for example, with the addition of heat above the polymer's glass transition temperature. In example embodiments, use of one or more thermoplastic polymers such as, but not limited to, poly(lactic acid) [PLA], poly (glycolic acid) [PGA], and/or poly(lactide-co-glycolide) [PLG] may result in thermally shapeable constructs. When exposed to temperatures above the glass transition point of the polymer, the scaffold becomes flexible and can be custom molded to fit the surgical site. The heating of the scaffold can be accomplished for example, by soaking the scaffold in hot water, or exposing the scaffold to a variety of heat sources such as hot air gun, microwave, or a heated shaping device. As the shaped scaffold quickly cools (whether subjected to cooling or allowed to cool to the surrounding temperature), the structure maintains its new modified shape and provides a custom fit. Devices in accordance with these embodiments may be used for example in methods where the device is heated to become flexible, placed into a desired position, and maintained in that position until a desired rigidity of the device is achieved.

One skilled in the art will appreciate that methods disclosed herein may be advantageous over methods of forming polymer scaffolds using solvent-based techniques which produce weaker foam structures having a greater number of micropores. In solvent-based techniques a polymer is dissolved in a solvent to create a gel. The solvent is slowly removed through a drying process and the result is a highly porous foam that has a broad pore size distribution. The large variety of pore sizes is due to the extraction of the solvent during the drying steps. As a polymer solution dries, the removal of the solvent creates macropores (50-1000 μm) as well as micropores (<50 μm). Although these micropores contribute to the overall percent porosity of the scaffold, they are too small for tissue in-growth and only weaken the polymer structure. In the thermal consolidation technique disclosed herein, a thermally stable material can be chosen with a high enough viscosity so that essentially only the large pores are coated. When the coated construct is heated to the melting temperature of the polymer, the microporous polymer phase will consolidate into a single phase with little to no microporosity. The reduction or elimination of the unusable microporosity may significantly improve the overall strength of the porous composite while maintaining the macroporosity of the scaffold.

Further encompassed by the present invention are implants comprised entirely of or partially of at least one porous or semi-porous, elastomeric scaffold, which scaffold may be made by any suitable technique. Such implants may include for example, one or more of the elastomeric materials described herein and/or any suitable elastomeric material known to those skilled in the art. Exemplary embodiments may include implants capable of supporting dynamic loading and/or implants that allow for soft tissue in-growth. With elastomeric properties and a porous or semi-porous structure, exemplary implants may be capable of supporting cyclic loading such as in the spine while allowing tissue growth into the implant device to form an interface that would reduce or prevent device migration. According to non-limiting exemplary embodiments, such implants may be adapted such that they are suitable for nucleus or disc replacement, and cartilage repair.

Also encompassed are methods of making implants comprised entirely of or partially of porous, elastomeric scaffolds, as well as kits and systems including such implants. Further encompassed are methods of treating a patient by inserting into a patient such an implant comprising at least one porous, elastomeric scaffold.

Devices Having Multiple-Phase Degradation Capabilities

The combination of two or more materials, for example in a scaffold or composite, may also offer improved degradation profiles and other properties such as tissue in-growth. Such materials may optionally include for example, two or more materials having different degradation profiles, such as those discussed further herein. By way of non-limiting example, devices may include three-dimensional scaffolds or composites made by the methods described herein, in which some particles in the scaffold comprise a composition having a first degradation profile, and other particles comprise a composition having a second degradation profile. Other example embodiments may include any devices having two or more materials having different degradation profiles, and may include devices comprising scaffolds, composites or other structures made by any suitable method.

Exemplary embodiments include a plurality of polymer particles bonded together to form a scaffold; where the plurality of polymer particles include particles having at least two different degradation profiles. The bonding may occur by any method known to those skilled in the art, and may include for example, at least one of cross-linking, melting, sintering, compressing, and other methods of forming chemical or physical bonds between the particles. Example embodiments include scaffolds that include a plurality of biodegradable particles having at least two different particles shapes or sizes; wherein the particles are bound together to form a scaffold.

According to example embodiments, particle scaffolds may be fabricated by providing a plurality of biodegradable particles, having at least two different degradation rates; and bonding the particles together (for example, by sintering) to form a scaffold. According to example embodiments, the particles may be subjected to the particle compression technique or the thermal consolidation technique.

By way of non-limiting example, particle scaffolds may be fabricated by providing a plurality of polymer particles comprising two or more resorbable polymers, wherein the plurality of particles comprise at least two polymers having at least two different degradation profiles; adding the plurality of particles to a mold or device; and sintering the particles together to form a scaffold. These methods may further include removing the mold, or removing the scaffold from the mold after sintering.

The polymer particles may include any of the polymers or combinations thereof discussed herein, and may be selected for example, based on their relative rate of degradation or other characteristics depending on the purpose for which the implant is being used. For example, suitable polymers may include at least one polymer selected from the group consisting of resorbable polymers, biocompatible polymers, and copolymers.

Exemplary embodiments of methods of making a device that includes a polymer particle scaffold may further include steps according to particle compression or thermal consolidation techniques discussed herein. For example, such methods may include subjecting the scaffold to a thermal consolidation process comprising coating the scaffold with a thermally stable material to produce a coated structure; and heating the coated scaffold past the melt temperature of the underlying polymer to thermally consolidate the underlying polymer scaffold. The thermally stable material may be as described herein with respect to other embodiments and may be removed or may be retained.

Accordingly, exemplary methods may include providing a plurality of polymer particles comprising one or more resorbable polymers; adding the plurality of particles to a structure; bonding the particles together to form a bonded particle structure having a porosity; at least partially filling the porosity of the particle structure with a thermally stable material; and heating past the melt temperature of the particle structure and under the melt temperature of the thermally stable material to thermally consolidate the particles. The structure may be a mold or implant for example.

Devices made using these example methods may be adapted for various uses. By way of non-limiting example, such devices may be adapted for use in one or more structural grafting applications selected from the group consisting of spinal fusion, fracture fixation, hip and knee arthroplasty, craniofacial reconstruction, and sports medicine applications.

In exemplary embodiments of devices that include a particle scaffold, the particles include first particles comprising a first composition comprising at least one polymer, wherein said first particles have a first resorption rate; and second particles comprising a second composition comprising at least one polymer, wherein said second particles have a second resorption rate. The first and second resorption rates are different. The particles may also include a third or more particles comprising a composition having at least one polymer with yet a different resorption rate.

Figure 4:
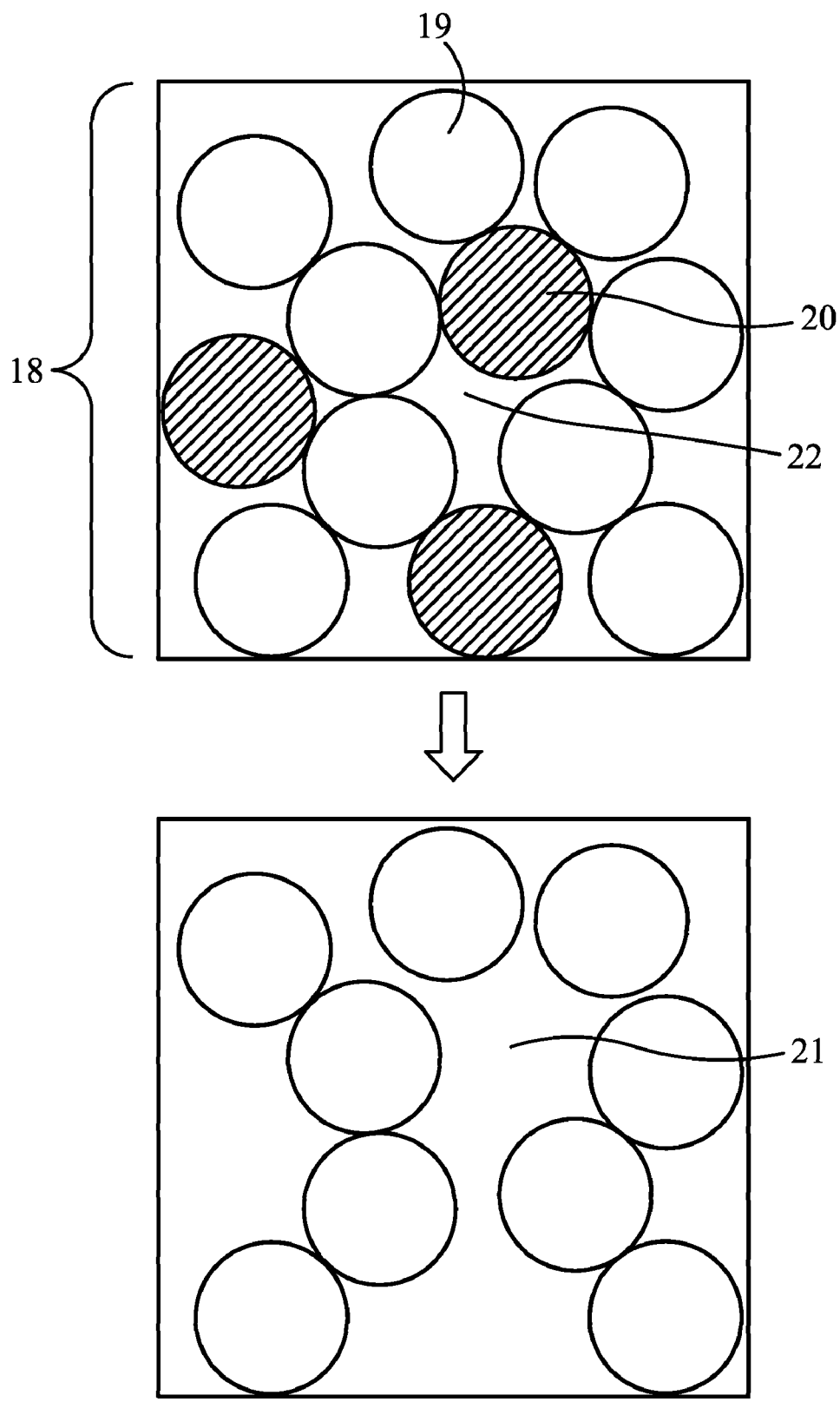
FIG. 4 is an illustration of the resorption of a two-phase particle scaffold in accordance with non-limiting example embodiments.

FIG. 4 depicts exemplary embodiments of a two-phase particle scaffold that can be created using particles created from two or more polymers having different resorption profiles. As depicted in FIG. 4, the three-dimensional structure 18 is created from a combination of a slow resorbing particles 19 and a fast resorbing particles 20. Once implanted, the fast resorbing particles are degraded first and result in a porosity 21, which is greater than the original porosity 22 of the original three-dimensional structure 18. This increase in porosity allows for additional tissue in-growth through the structure.

An advantage over conventional scaffold techniques is that the structure of exemplary embodiments has sufficient initial mechanical strength to survive implantation but then has an increasing porosity as it is resorbed. Once implanted, the strength may no longer be needed and porosity increases as the fast phase is resorbed. This new greater porosity allows for additional tissue in-growth through the scaffold. As tissue regeneration progresses, more and more of the porosity is filled with new tissue. Unlike conventional scaffolds, as the porosity of a two or more phase structure is filled with tissue, more porosity is created as the quickly degrading particles are resorbed by the body. This type of stepwise resorption profile allows the implant to possess mechanical properties suitable for implantation but also an increasing ability to support tissue in-growth as the fast resorbing phase is removed.

Further control over strength and porosity can be achieved by using several different materials. This will allow the scaffold's strength-resorption profile to be tailored specifically for each surgical application.

In exemplary embodiments, various forms of the same polymer, poly (lactide-co-glycolide), may be used to give particles with varying degradation profiles. The copolymer 82:18 poly (L-lactide-co-glycolide) has been shown to have a degradation time of 6-9 months while 85:15 poly (D,L lactide-co-glycolide) degrades in 2-3 months. In exemplary embodiments, these polymer may be formed into microspheres and then combined in a range of about 95:5 to 5:95 depending on the desired resorption profile. In other example embodiments, the ratio may be about 80:20 or 50:50 slow resorbing polymer to fast resorbing polymer.

In other exemplary embodiments, loose slow degrading (SD) particles and loose fast degrading (FD) particles may be mixed to create an essentially even dispersion of FD particles amongst the SD particles. The mixture may then be added to a mold and bonded (e.g., sintered) to create a three-dimensional particle structure. The structure could then be subjected to the particle compression technique or the thermal consolidation technique described herein to further improve the mechanical properties of the scaffold. In the resulting scaffold, the FD spheres would be resorbed in a period of approximately 2 to 3 months, while the SD spheres would be resorbed in approximately 6 to 9 months. Additionally, variations in the molecular weight (inherent viscosity or "IV") of the same polymer can be used to create varying degradation profiles. For example, fast resorbing, low molecular weight PLG polymer with an IV range of 0.5-1.5 can be mixed with slower resorbing, high molecular weight PLG with an IV range of 4-7.

In other example embodiments, different polymers can be used to create the scaffold. In these embodiments, slower resorbing 70:30 poly (L/D,L lactide) particles could be mixed with faster resorbing 82:18 poly(lactide-co-glycolide) particles to create a step-wise resorption.

Also included are composites comprising a plurality of portions; where at least two portions of the plurality of portions have different degradation profiles. According to these embodiments, two or more phase composites may be formed that degrade in a manner that allows for eventual tissue in growth. In particular, a goal with creating such a composite is that the eventual resorption of a fast degrading phase will allow space for tissue in-growth. For example, a multi-phase composite can be created by embedding one or more faster degrading particles, e.g., fibers, rods or other shapes made of a faster resorbing material into a substrate made of a slower resorbing material. There may be more than one fast degrading particle, which may have the same or different resorption properties from one another. Additionally, a multi-phase composite can be created by creating a plurality of spaces independent from one another in a solid piece of a first material and filling said spaces with one or more second materials that has a different resorption profile. A non-limiting example of a two-phase composite is described in Example 3.

The faster degrading region may span from a first side of the substrate to a second side of the substrate. The first and second sides may be adjacent to one another or opposite one another, or in the case of rounded substrates, where there is only one side, the so-called first and second sides are different areas of the rounded portion. Spanning from a first side to the second side means that either a portion of the fast degrading region is exposed on one or both or more sides, or it may mean that ends of the fast degrading region may be sufficiently close to the sides, such that the composite may be machined to expose at least one surface of the fast degrading particle. Embodiments where the fast resorbing region has a length sufficient to span across the composite, allows for continuous tissue in-growth from one side to the other. In example embodiments, the fast degrading particle may span to more than two sides of the substrate.

The fast degrading (FD) particle may comprise any number of a variety of shapes, such as a fibers, rods, blocks or other shapes that may allow the fast resorbing phase to span one side of the composite to the other. Additionally, three-dimensional fiber structures created from 3-D braids, weaves or meshes can be embedded in a slow resorbing substrate to create a fiber reinforced composite. Although these fibers may not be bonded together into a continuous phase, when the composite is machined into an implant, the individual fiber ends are exposed at both ends allowing for resorption and eventual tissue in-growth from one side of the composite to the other. In example embodiments, FD rods may be embedded in slow degrading (SD) substrates using injection molding or melt processing techniques. In other example embodiments, a three-dimensional fiber braid of FD may be embedded in a SD substrate using injection molding or melt processing.

Accordingly, example embodiments include a resorbable structural composite comprising at least one fast degrading particle within a slower degrading substrate having at least a first side and a second side; wherein the fast degrading particle has a length sufficient to span from a first side of the composite to a second side of the composite. Methods for creating resorbable structural composites may include for example, embedding at least one fast degrading particle within a slower degrading substrate, wherein the substrate has at least a first side and a second side, to create a composite. Composites may be machined into a device such as a plate, rod, screw (such as a fracture or interference screw), intervertebral spacer, suture anchor, or tack.

Example methods of making a resorbable structural composite may include creating openings within a slower degrading substrate, wherein the substrate has at least a first side and a second side; and filling one or more of the openings with one or more faster degrading materials to create a composite. The openings may be created for example by one or more methods selected from the group consisting of drilling, milling, melting, etching, and dissolution.

According to example embodiments the slower degrading material may be a biocompatible, bioabsorbable polymer or copolymer. Example faster degrading material may include a calcium cement, such as those selected from calcium sulfate, calcium phosphate, and calcium carbonate.

Additional example embodiments include a solid material that is machined, drilled, or otherwise modified to create open spaces in the solid material. Other materials with different resorption rates may then be added to the open spaces to fill or partially fill the space. The spaces may completely or partially span across the first material. This is shown in FIG. 5.

Figure 5:
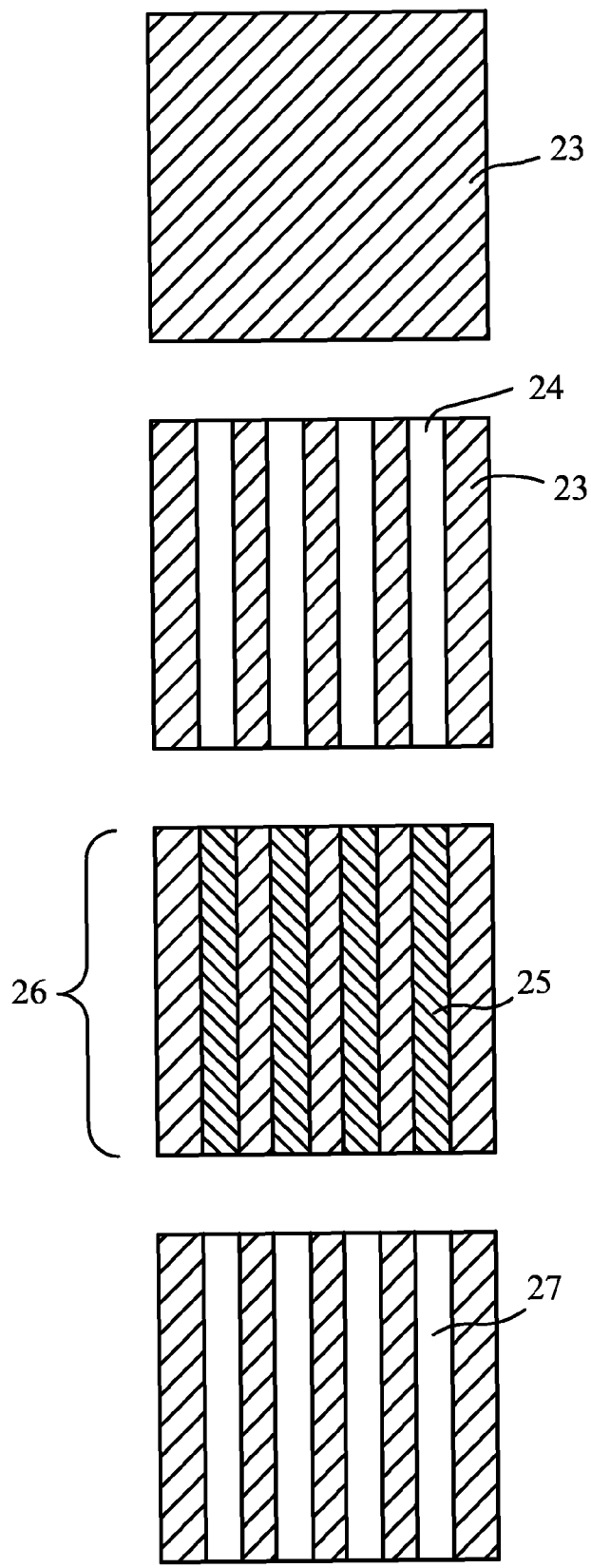
FIG. 5 is an illustration of a two-phase composite in accordance with non-limiting example embodiments.

FIG. 5 depicts a multi-phase composite in accordance with non-limiting example embodiments. The composite may be created by machining a slow resorbing material 23 and creating open spaces 24. The spaces are then filled in with a fast resorbing material 25 resulting in a solid composite 26. The composite 26 depicted in FIG. 5 has the ability for tissue in-growth as the fast resorbing phase is degraded. In the embodiments depicted in FIG. 5, fast resorbing regions 25 are embedded in a slow resorbing polymer 23. If portions of the fast resorbing material are not already exposed, according to example embodiments, the composite can be machined to expose at least one surface of the fast resorbing materials and allow for tissue in-growth into the composite. When this composite is implanted in tissue, the resorption of the fast phase will allow for porosity 27 to develop within the composite. This newly open porosity will allow for tissue in-growth into the composite.

It may be advantageous with respect to tissue in-growth for the fast resorbing phase to span the width of the composite as depicted in FIG. 5. Although the regions are not bonded to one another in a continuous phase, they may be exposed on both sides of the composite. This allows for tissue in-growth from either side of the implant.

Also encompassed are implants made in whole or in part of such composites. Implants may be adapted for many possible applications. In particular, such composites and implants made therefrom may be suitable for surgical applications, including, but not limited to spinal interbody fusion, fracture fixation (such as plates and screws), and structural grafting where load resistance is required throughout healing. Other non-limiting examples of suitable applications may include suture anchors, tacks, staples, interference screws, bone fusion, bone augmentation, sports medicine, orthopaedic trauma, hip and knee replacement and sports medicine. An advantage of the multi-phase composite over other implant materials is that it allows for the in-growth of tissue into the composite while still providing mechanical support to the site.

Kits

Example embodiments of the present invention are further directed to kits that include at least one of the scaffolds, composites or devices that include scaffolds, or composites of the present invention.

Numerous possible additions to kits may be contemplated by those skilled in the art reviewing this disclosure. For example, kits may further include one or more other devices, tools, materials, and the like that may be useful in conjunction with the scaffolds, composites or devices of the present invention. According to example embodiments, kits may include one or more devices, tools, materials and the like which may assist in inserting the implant into a patient and/or extracting the implant from a patient.

In embodiments where a scaffold is heated such that it becomes moldable, a kit may include a device for heating and/or cooling the scaffold at a desired time in the process of inserting the scaffold into a patient.

Kits may include tools or devices that may be useful in preparing a patient for insertion of the device into the patient.

Kits may also include one or more devices useful in placement or shaping of the device. For example, kits may include at least one component for visualizing the device within a patient, before, during and/or after placement.

Kits may include ingredients for making scaffolds, composites or devices in accordance with the present invention. For example, kits may include polymer particles, molds, scaffolds, rods, and the like, and may further include means for bonding (e.g., by sintering), compressing or performing any the methods encompassed by the invention.

Kits may include materials for adding biological activity to the devices. For example, kits may include growth factors solutions or powders, marrow aspiration needles, demineralized bone matrix powder, or other materials that may improve the healing of the device.

Systems

Exemplary embodiments of the present invention are further directed to systems that include at least one scaffold, composite or devices including such scaffolds or composites of the present invention. Such systems may additionally include one or more other devices, tools, materials, and the like that may be useful in conjunction with the scaffolds, composites or devices of the present invention.

Systems may include one or more devices disclosed herein and means for visualizing the device during and/or after implantation into a patient.

Methods of Treating a Patient

Exemplary embodiments are further directed to methods of treating a patient, which include inserting into a patient in need of treatment, a device, such as the devices described herein. The term "patient" is intended to include any animal, including, but not limited to humans. For example, methods of treatment may include veterinary applications. Those skilled in the art would be able to ascertain, which animals may be treated by the various methods.

The reference to patients in "need of" treatment is intended to encompass situations in which treatment is medically necessary, as well as where treatment is medically advisable, or where treatment is desired but optional.

The following examples illustrate non-limiting embodiments. The examples set forth herein are meant to be illustrative and should not in any way serve to limit the scope of the claims. As would be apparent to skilled artisans, various changes and modifications are possible and are contemplated and may be made by persons skilled in the art.

Example 1

In this example, the method for creating a compressed microsphere implant is described. Poly (L/D,L lactide) is processed into microspheres with a size range of 600-850 μm. Loose spheres are placed in a mold and compressed to approximately 20% of their original height. The mold is locked and the approximately 20% height reduction is maintained. The compressed mold is then placed in an oven for sintering. Following heating, the mold is allowed to cool and the implant is removed from the mold. The compressed structure is now thermally bonded together and retains it sintered shape and the 20% compressed size. Additionally, the loose spheres can be placed in a mold outfitted with a piston and a piston stop. The stop can be set at approximately 20% of the original height of the loose packed spheres. During heating, the spheres soften and the weight of the piston compresses the spheres. The piston stop prevents the piston from compressing the sphere more than 20%. Once the spheres are fully compressed, the mold is cooled. Again, the compressed structure is now thermally bonded together and retains it sintered shape and compressed size.

Example 2

Figure 6:
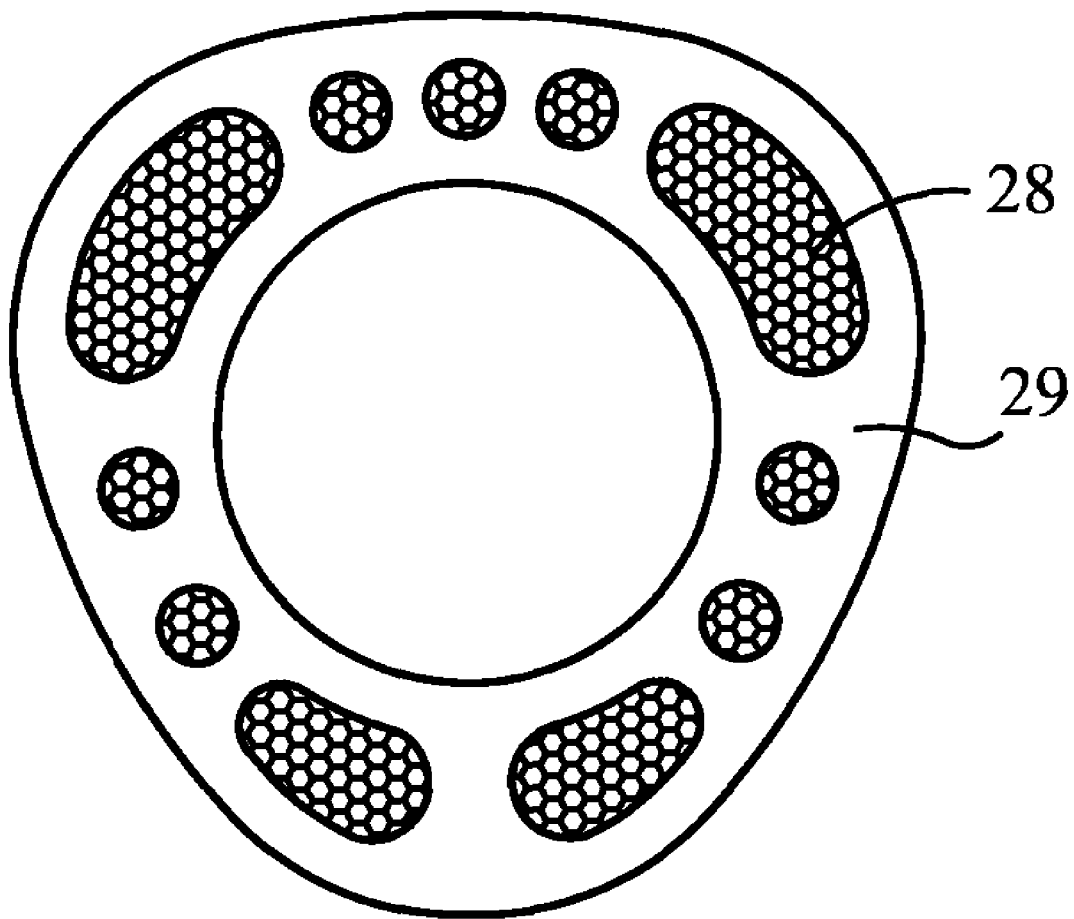
FIG. 6 is an illustration of an implant having a particle scaffold therein in accordance with non-limiting example embodiments.

In this example, an embodiment is depicted in FIG. 6 in which multiple resorbable polymer microsphere scaffolds 28 are formed within an implant 29. The implant itself is also resorbable, and may be any number of different implants. In this particular example an intervertebral fusion implant is depicted. The implant is composed of PLA polymer has openings machined into the implant wall. The microsphere scaffolds may be formed in these openings in accordance with methods of the invention. In particular, a PLA intervertebral implant is placed in a mold. Loose microspheres comprised of an approximately 50:50 mix of 82:18 poly (L-lactide-co-glycolide) and 85:15 poly (D,L lactide-co-glycolide) are poured into the openings with the wall of the PLA implant. Once the openings are filled, the mold containing the PLA implant and loose sphere is placed in the oven to sinter the spheres to one another and also to the PLA implant walls. Once heating is complete, the implant is removed from the mold and the implant walls are now filled with a sintered multi-sphere scaffold.

Example 3

In this example, the method for creating a two-phase structural composite is described. A solid block of 70:30 poly (L/D,L lactide) is machined to create a resorbable intervertebral implant. A variety of holes are drilled through the solid implant to create open channels. The channels are then filled with a fast resorbing calcium ceramic cement (2-3 month resorption time). Once the cement hardens, the composite is further machined into its final implant form. The resulting structure consists of discreet polymer and ceramic phases.

Although the invention has been described in example embodiments, many additional modifications and variations would be apparent to those skilled in the art. For example, many modifications may be made by those skilled in the art to the example implants. Other modifications may be made for example to the methods, including the addition of or changing the order of various steps. It is therefore to be understood that this invention may be practiced other than as specifically described. Thus, the present embodiments should be considered in all respects as illustrative and not restrictive.

What is claimed is:

1. A device comprising
   a three-dimensional porous scaffold comprising compressed and sintered resorbable microspheres, made by a method comprising:
   providing a plurality of resorbable microspheres;
   compressing the microspheres together; and thereafter
   sintering the microspheres together to form a scaffold.

2. The device of claim 1, wherein said device is an interbody spacer.

3. A porous implant comprising a porous scaffold comprising a plurality of compressed and thereafter sintered resorbable polymer microspheres.

4. A kit comprising
   the porous implant of claim 3; and
   at least one device for placement or shaping of the porous implant in a patient.

5. The porous implant of claim 3, wherein said implant is rigid or semi-rigid.

6. The porous implant of claim 3, wherein said implant is in a form selected from the group consisting of a granule, a sheet, a rod, and a block.

7. The porous implant of claim 3, wherein the porous implant is a fusion device.

8. The porous implant of claim 7, wherein said fusion device is a spinal interbody fusion device.

9. The porous implant of claim 7, wherein said fusion device is a foot and ankle fusion device.

10. The porous implant of claim 3, wherein the porous implant is a bone graft.

11. The porous implant of claim 3, wherein the porous implant is an interbody spacer.

12. A kit comprising
    the porous implant of claim 3; and
    at least one device for visualizing the porous implant within a patient.

13. A kit comprising
    the porous implant of claim 3; and
    at least one material for adding biological activity to the porous implant.

14. The kit of claim 13, wherein the at least one material for adding biological activity to the porous implant is selected from the group consisting of growth factors, antibiotic substances, cells, blood factors, marrow aspiration needles, and demineralized bone matrix powder.

15. A three-dimensional scaffold comprising:
    a plurality of homogeneously mixed biodegradable microspheres having at least two different degradation rates;
    wherein the microspheres are bound together to form a scaffold.

16. The three-dimensional scaffold of claim 15, wherein said three-dimensional scaffold is rigid or semi-rigid.

17. The three-dimensional scaffold of claim 15, wherein said three-dimensional scaffold is in a form selected from the group consisting of a granule, a sheet, a rod, and a block.

18. The three-dimensional scaffold of claim 15, wherein the three-dimensional scaffold is a fusion device.

19. The three-dimensional scaffold of claim 18, wherein said fusion device is a spinal interbody fusion device.

20. The three-dimensional scaffold of claim 18, wherein said fusion device is a foot and ankle fusion device.

21. The three-dimensional scaffold of claim 15, wherein the three-dimensional scaffold is a bone graft.

22. A kit comprising
    the three-dimensional scaffold of claim 15; and
    at least one device for placement or shaping of the three-dimensional scaffold in a patient.

23. A kit comprising
    the three-dimensional scaffold of claim 15; and
    at least one device for visualizing the three-dimensional scaffold within a patient.

24. A kit comprising
    the three-dimensional scaffold of claim 15; and
    at least one material for adding biological activity to the three-dimensional scaffold.

25. The kit of claim 24, wherein the at least one material for adding biological activity to the three-dimensional scaffold is selected from the group consisting of growth factors, antibiotic substances, cells, blood factors, marrow aspiration needles, and demineralized bone matrix powder.

26. A device comprising
    at least one three-dimensional scaffold comprising a thermally-consolidated microsphere scaffold made by a method comprising:
    coating a porous microsphere scaffold with a thermally stable material; and
    heating the coated scaffold to a temperature above melt temperature of the scaffold and under melt temperature of the thermally stable material, to thermally consolidate the scaffold.

27. The device of claim 26, wherein said coating comprises filling essentially the entire porosity of the microsphere scaffold with a thermally stable material.

28. The device of claim 26, wherein said coating comprises coating the surface of the microsphere scaffold while essentially retaining the scaffold's porosity.

29. An implant comprising at least one porous or semi-porous, elastomeric scaffold, wherein said scaffold consists essentially of bonded elastomeric microspheres.

30. The implant of claim 29, wherein the implant is adapted for nucleus or disk replacement.

31. The implant of claim 29, wherein the implant is adapted for cartilage repair.

32. The implant of claim 29, wherein the implant is adapted for soft tissue augmentation.

33. The implant of claim 29, wherein said elastomeric microspheres comprise at least one material selected from the group consisting of silicone, hydrogels, and polyurethane.

* * * * *